United States Patent
Bhasin (10) Patent No.: US 11,682,494 B2
(45) Date of Patent: Jun. 20, 2023

(54) METHOD AND APPARATUS FOR GENERATING HEALTH INDICATOR DATA

(71) Applicant: VISA INTERNATIONAL SERVICE ASSOCIATION, San Francisco, CA (US)

(72) Inventor: Gurpreet Singh Bhasin, Foster City, CA (US)

(73) Assignee: Visa International Service Association, San Francisco, CA (US)

( * ) Notice: Subject to any disclaimer, the term of this patent is extended or adjusted under 35 U.S.C. 154(b) by 850 days.

(21) Appl. No.: 16/218,055

(22) Filed: Dec. 12, 2018

(65) Prior Publication Data

US 2020/0194122 A1 Jun. 18, 2020

(51) Int. Cl.
*G16H 50/30* (2018.01)
*G06Q 20/32* (2012.01)
*H04L 67/50* (2022.01)

(52) U.S. Cl.
CPC ......... *G16H 50/30* (2018.01); *G06Q 20/3221* (2013.01); *H04L 67/535* (2022.05)

(58) Field of Classification Search
CPC ........ G06F 40/20; G06F 40/30; G06F 40/117; G06F 16/93; G06F 16/9535; G06F 16/24578; G16H 40/20; G16H 50/00; G16H 80/00; G16H 10/60; G16H 50/70; G16H 15/00; G06Q 30/0233; G06Q 20/29
See application file for complete search history.

(56) References Cited

U.S. PATENT DOCUMENTS

| 8,560,344 B2 * | 10/2013 | Earles | G06Q 30/02 705/2 |
| 2015/0127476 A1 * | 5/2015 | Skiba | G06Q 20/3574 705/17 |
| 2015/0269346 A1 * | 9/2015 | Lee | G06Q 30/0255 705/14.53 |

* cited by examiner

*Primary Examiner* — Eliza A Lam (74) *Attorney, Agent, or Firm* — K&L Gates LLP (57) ABSTRACT

An apparatus and method is disclosed for generating health indicator data such as behavioral health indicators, de facto health indicators, and composite health indicators. Behavioral health indicators represent a degree to which the one or more persons associated with the payment transaction data make health-conscious decisions and are generated based on payment transaction data. Behavioral health indicators may also be generated using a food behavior health indicator, a lifestyle health indicator, an activity health indicator, and a body metric health indicator. De facto health indicators represent a degree to which the one or more persons are observably healthy and are generated based on health sector data. Composite health indicators represent a holistic and complete picture of current and future health and are generated based on behavioral health indicator and de facto health indicator.

17 Claims, 3 Drawing Sheets

METHOD AND APPARATUS FOR GENERATING HEALTH INDICATOR DATA

BACKGROUND

The present disclosure relates to apparatus and methods for the generation of health indicator data, and more particularly to apparatus and methods for the generation of health indicator data based on payment transaction data.

SUMMARY

A method and apparatus for generating health indicator data is disclosed. In one embodiment, the method and apparatus may include consumer identification logic and behavioral health indicator generation logic. During a payment transaction (e.g., a payment card transaction) a payment mechanism (e.g., a credit card) is used to purchase one or more items (e.g., food, beverages, merchandise, services) and payment transaction data (e.g., credit card transaction data) is generated (e.g., by a merchant or merchant acquiring bank). Based on the payment transaction data, the consumer identification logic generates consumer ID data identifying a person(s) associated with the payment mechanism and the behavioral health indicator generation logic generates a behavioral health indicator for the associated person(s). The behavioral health indicator (e.g., a score) represents a degree to which the associated person(s) makes health-conscious decisions.

In one embodiment, the payment transaction data is stored in a historical database as historical payment transaction data or the behavioral health indicator is stored in the historical database as an historical behavior heath indicator. As the person(s) associated with the payment mechanism enter into a new payment transaction, thereby generating new payment transaction data, the behavioral health indicator generation logic may generate an updated behavioral health indicator based on the new payment transaction data and the historical payment transaction data or the historical behavioral health indicator. The updated behavioral health indicator represents an updated degree to which the one or more persons make health-conscious decisions.

In another embodiment, the method and apparatus includes de facto health indicator generation logic and composite heath indicator generation logic. The de facto health indicator generation logic generates a de facto health indicator based on health sector data and the consumer ID data. The health sector data may be health care consumption data representing a degree to which the person(s) identified in the consumer ID data has received/used health care services from health care providers (e.g., a dollar value or number of doctor appointments/visits) or heath care evaluation data representing results of health care provider-administered examination of the person(s) identified in the consumer ID data. The de facto health indicator represents a degree to which the person(s) are observably healthy (e.g., from the perspective of the heath sector insurance and medical providers). Composite health indicator generation logic then provides a composite view of the person(s) health based on the behavioral health indicator and/or updated behavior indicator and the de facto heath indicator.

In one embodiment, the method and apparatus includes privacy logic that generates privacy control data based on opt-in request data generated by a user (e.g., through a graphical user interface or a health tracking device such as a FitBit, Apple Watch, Garmin Fenix, Samsung Wear, etc.). The behavioral health indicator generation logic communicates the behavior heath indicator and updated behavioral health indicator to third parties (e.g., a third-party controlled composite health indicator generation logic) based on the privacy control data.

BRIEF DESCRIPTIONS OF THE DRAWINGS

The detailed description refers to the following figures in which.

DETAILED DESCRIPTION

Figure 1:
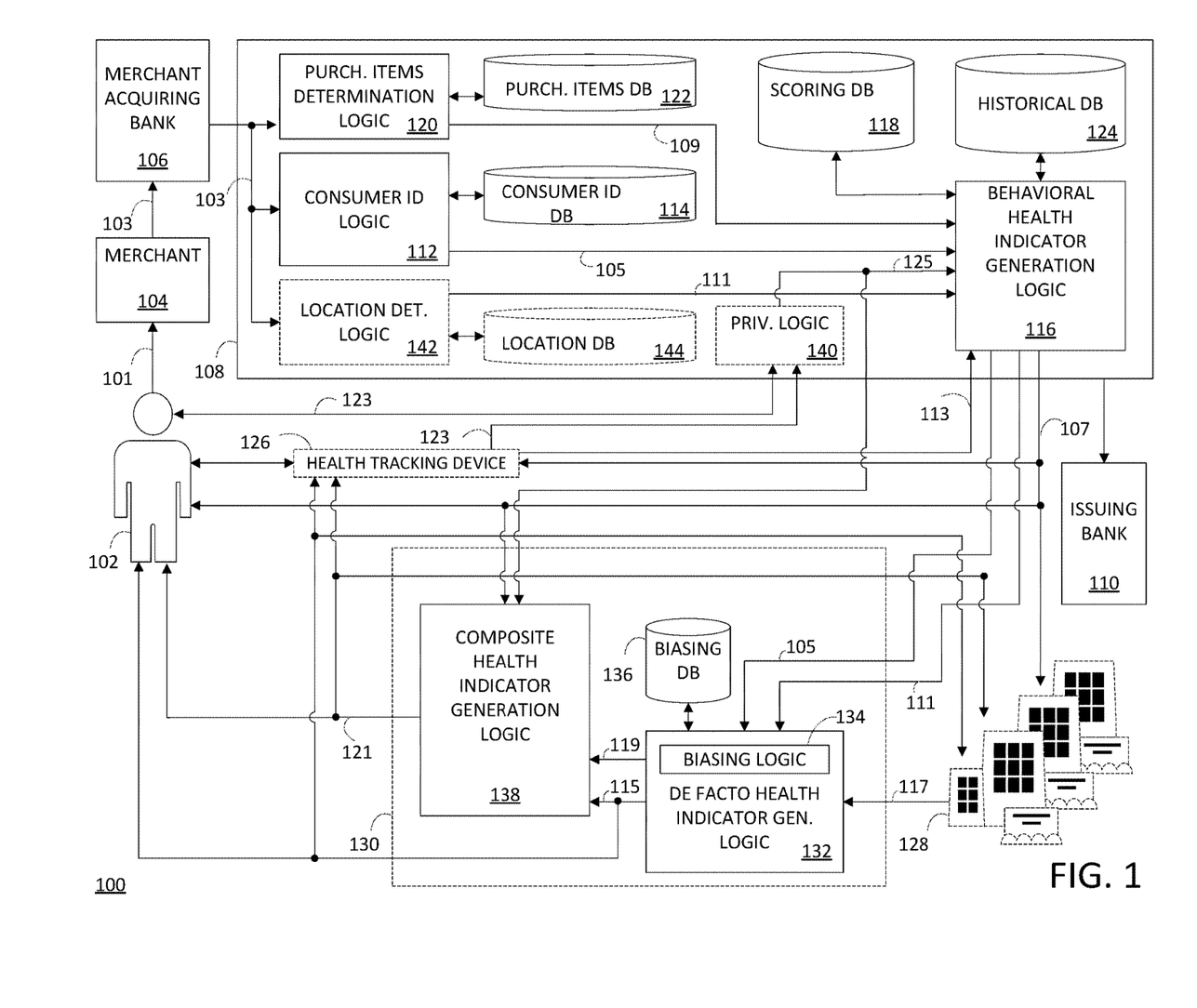
FIG. 1 is a schematic block diagram depicting an example of apparatus for generating health indicator data and in particular behavioral health indicator, de facto health indicator, and composite health indicator in accordance with one embodiment of the present disclosure.

FIG. 1 is a schematic block diagram 100 depicting an example of apparatus for generating health indicator data and in particular behavioral health indicator 107, de facto health indicator 115, and composite health indicator 121. When a user 102 enters into a payment transaction with a merchant 104 to purchase one or more items (e.g., food, beverages, merchandise, and/or services) by submitting or using 101 an electronic or digital payment mechanism (e.g., payment card, bit coin, etc.), payment transaction data 103 is generated as part of a payment process. Merchant 104 may be a physical brick and mortar merchant or an on-line merchant that uses a physical or virtual merchant payment terminal (e.g., a payment card reader, a virtual wallet reader, and/or a payment page on a website).

In an embodiment where the payment mechanism is a payment card (e.g., a consumer credit card, a corporate credit card, a business credit card, or a government credit card), merchant 104 generates payment transaction data 103 and communicates it to a merchant acquiring bank 106. In turn, merchant acquiring bank 106 communicates payment transaction data 103 to an electronic payments authorization network 108 such as VisaNet or the MasterCard Network. For each payment transaction, the electronic payments authorization network 108 processes the associated payment transaction data 103, checks the card security features, determines the cardholder's issuing bank and sends the payment transaction data 103 to the cardholder's issuing bank 110 for transaction approval. The issuing bank 110 decides whether to approve the payment transaction and sends its approval or disapproval message back to the merchant acquiring bank 106 via the electronic payments authorization network 108. In turn, the merchant acquiring bank 106 sends the approval or disapproval message back to the merchant 104. If approved, the user 102 completes the payment transaction with merchant 103.

In one embodiment, electronic payments authorization network 108 includes consumer identification logic 112, consumer ID database 114, behavioral health indicator generation logic 116, and scoring database 118. Consumer identification logic 112 generates consumer ID data 105 based on payment transaction data 103. Consumer ID data 105 identifies one or more persons associated with the payment mechanism used in the payment transaction. In one embodiment, consumer identification logic 112 processes payment transaction data 103 to directly identify such persons (e.g., the identity of such persons is set forth in the payment transaction data 103) or indirectly identify such persons (e.g., consumer identification logic 112 looks up such persons using indexing data set forth in the payment transaction data 103). For example, where payment transaction data 103 is payment card transaction data, consumer identification logic 112 processes payment card transaction data to obtain data associated with one or more of the following fields in the payment card transaction data: first name, last name, zip code, billing address, and shipping addresses data fields. In one embodiment, the data in these fields are used to query consumer ID database 114 to uncover the identity of the one or more persons.

Behavioral health indicator generation logic 116 generates behavioral health indicator 107 for the one or more persons associated with the payment mechanism used in the payment transaction based on payment transaction data 103. Behavioral health indicator 107 represents a degree to which the person(s) make health-conscious decisions. In one embodiment, behavioral health indicator 107 represents the degree to which the one or more purchase items are considered to be healthy or unhealthy. And in one embodiment, behavioral health indicator 107 takes the form of a numerical score. In one embodiment, behavioral health indicator generation logic 116 uses information contained in the payment transaction data 103 to query the scoring database 118, and uses the result of that query to generate behavioral health indicator 107.

In one embodiment, electronic payments authorization network 108 includes purchased items determination logic 120 and purchased items database 122. Purchased items determination logic 120 generates purchased items ID data 109 based on payment transaction data 103. Purchased items ID data 109 identifies whether one or more items in the payment transaction constitute food or beverage items, or conversely whether the one or more items in the payment transaction constitute non-food or beverage items such as other merchandise and services. Purchased items ID data 109 may also identify each item by product name and size. In an embodiment where the payment transaction data 103 is payment card transaction data, for example, purchased items ID determination logic 120 ascertains the UPC code, Global Trade Item Number (GTIN) data or other identifying data about each item from the payment card transaction data. In one embodiment, the purchased items ID data 109 is ascertainable from the UPC code, GTIN data, or other identifying data (e.g., by application of an algorithm that correlates purchased items ID data based on the content of the UPC code, GTIN data, or other identifying data). In another embodiment, the UPC code, GTIN data, or other identifying data is used (e.g., as an index) by Purchase items determination logic 120 to query purchased items database 122 to obtain purchased items ID data 109.

The three largest electronic payment authorization networks 108 as of the filing date are associated with the Visa, MasterCard and American Express payment card companies. Data processing over these electronic payment authorization networks 108 is typically grouped into one of three layers or data rates. Visa and American Express use Levels I-III (also known as Levels 1-3) and MasterCard uses Data Rates I-III (also known as Data Rates 1-3). Generally, consumer payment card transactions are processed in accordance with Level I/Data Rate I. And certain corporate, business, and/or government payment card transactions are processed in accordance with Levels II or III/Data Rates II and III. Payment transaction data 103 associated with Level I/Data Rate I transactions include the least amount of data fields, whereas more data fields are available in payment transaction data 103 associated with Level II/Data Rate II and even more data fields are available in payment transaction data 103 associated with Level III/Data Rate III. The specific fields that are mandatory and optional at each level or rate are set by the payment specifications issued by each payment card company and are subject to change. At present, Level III/Data Rate III payment transaction data 103 includes data fields capable of identifying a UPC code, GTIN data, or other identifying data.

Figure 2:
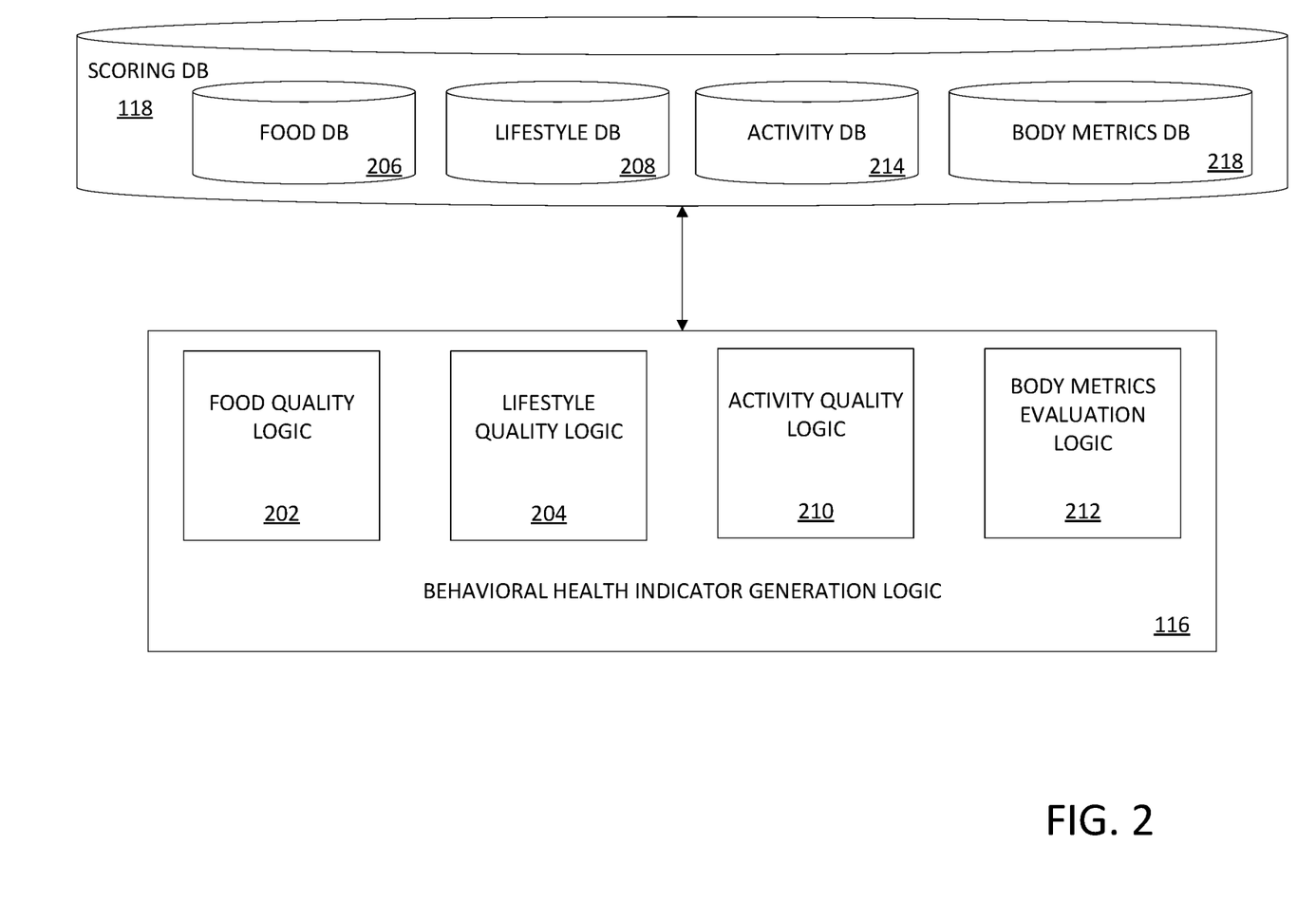
FIG. 2 is a schematic block diagram depicting an exemplary behavioral health indicator generation logic and exemplary scoring database of FIG. 1 in accordance with another embodiment of the present disclosure.

With reference to FIG. 2, behavioral health indicator generation logic 116 may include food quality logic 202 and lifestyle quality logic 204 and scoring database 118 may include food database 206 and lifestyle database 208. Each of the food quality logic 202 and the lifestyle quality logic 204 receives purchased items ID data 109 and generates health indicators based thereon. In particular, if an item in the one or more purchased items is determined to be a food or beverage item, then food quality logic 202 generates a food health indicator representing the degree to which the item represents a health-conscious purchase. Similarly, if an item is determined to be neither a food item nor a beverage item, the lifestyle quality logic 204 is operative to generate a lifestyle health indicator representing a degree to which the item is associated with an active lifestyle. In each case, the food quality logic 202 and the lifestyle quality logic 204 generate the indicators based at least on the purchased item ID data 109. In one embodiment, purchase items ID data 109 is used to query food data base 206 and lifestyle database 208 to generate these indicators. Alternatively, query results are used by the food quality logic 202, lifestyle quality logic 204, and/or other logic associated with the behavioral health indicator generation logic 116 to generate the food health indicator and the lifestyle health indicator.

Returning to FIG. 1, in one embodiment, the electronic payment authorization network 108 further includes location determination logic 142 and location database 144. Location determination logic 142 generates location ID data 111 based on payment transaction data 103. Location ID data 111 identifies the physical location associated with each payment transaction using for example, the point of sale terminal location data field in payment card transaction data (if the payment mechanism is a payment card). In one embodiment, location ID data 111 represents other physical locations (e.g., the location of the ship to address, the location of the billing address, etc.). Location database 144 may be queries by location determination logic 122 to obtain location ID data 111 and/or to store location ID data 111 once determined.

In one embodiment, the food health indicator generated by the food quality logic 202 is based on one or more of the nutritional value of the item (e.g., caloric content, sugar content, etc.), the size of the item, the frequency with which the item is purchased by the person(s) (e.g., as may be stored in historical database 124, as described below), the number of persons associated with the payment mechanism (e.g., as identified in the consumer ID data 105), the physical location of the each payment transaction (e.g., as identified in the location ID data 111), and a type of merchant where each payment transaction was made. For example, candy and soft drinks may receive quantitatively or qualitatively lower food behavioral health indicators than fruits and pomegranate juice.

And in one embodiment, the lifestyle health indicator is based on one or more of the size of the item, the frequency with which the item is purchased by the one or more persons associated with the payment mechanism (e.g., as may be stored in historical database 124, as described below), the physical location of the each payment transaction (e.g., as identified in the location ID data 111), and a type of merchant where each payment transaction was made. For example, if a person has been historically purchasing pants with a 32-inch waist size and then starts to regularly purchase pants with a 34-inch or 36-inch waist size, then the lifestyle health indicator will be quantitatively or qualitatively lower than if the person continues to purchase pants with a 32-inch size waist. In another example, if a person regularly purchases sporting apparel or pays monthly dues at a gym membership, the lifestyle behavioral health indicator may be quantitatively or qualitatively higher than if a person does not regularly purchase such apparel or pay dues at a gym.

The behavioral health indicator 107 is then generated by the behavioral health indicator generation logic 116 using one or more of the food health indicator and the lifestyle health indicator.

In one embodiment, the electronic payments authorization network 108 includes historical database 124 to store a first payment transaction data 103 associated with the payment transaction described above as historical payment transaction data or to store the behavioral health indicator 107 as historical behavioral health indicator. When new payment transaction data 103 associated with a new payment transaction is processed by merchant 104 and/or merchant acquiring bank 106, behavioral health indicator generation logic 116 generates an updated behavioral health indicator based on the new payment transaction data (e.g., based on new purchased items ID data 109, new consumer ID data 105, and/or new location ID data 111) and the historical payment transaction data and/or historical behavioral health indicator stored in historical database 124. The updated behavioral health indicator represents an updated degree to which the person(s) makes health-conscious decisions.

In one embodiment, user 102 may be associated with and wear or possess a health tracking device 126. Behavioral health indicator generation logic 116 may include activity quality logic 210 and body metrics evaluation logic 212, and scoring database 118 may include activity database 214 and body metrics database 218. Health tracking device 126 may generate activity data and/or body metric data 113 based on the user's activity level (e.g., steps taken, miles walked, stairs climbed, minutes of exercise, exercise type, frequency of standing, hours of sleep etc.) and body metrics (e.g., resting heart rate, active heart rate, irregular heart rate, etc.). Activity quality logic 210 and body metrics evaluation logic 212 receive activity data and body metric data, respectively, 113 and generate activity health indicator and body metric health indicator based thereon. Activity health indicator represents a degree to which an activity level associated with the person is consistent with health-conscious decisions. Similarly body metrics health indicator represents a degree to which one or more body metrics associated with the person is consistent with health-conscious decisions. Activity health indicator and body metrics health indicator may be based on the degree to which current and/or historical activity data and body metric data meet or exceed one or more predetermined thresholds as stored in activity database 214 and body metrics database 218. In such an embodiment, the behavioral health indicator 107 is generated using the activity health indicator and the body metric health indicator. For example, behavioral health indicator 107 may be based on food health indicator, lifestyle health indicator, activity health indicator, and body metric health indicator.

In one embodiment, behavioral health indicator generation logic communicates behavioral health indicator 107 with health sector providers 128 such as health insurance companies and health care providers. Health insurance companies might use the behavioral health indicator 107 to incentivize health care consumers to make health-conscious decisions by, for example, lowering premiums for those consumers whose behavioral health indicator 107 indicate that such consumers regularly make health-conscious decisions. And health care providers (e.g., internists, primary care physicians, etc.) may supplement a patient's medical record so that the providers might better diagnose and/or monitor patient progress toward a doctor's recommendation or order (e.g., to reduce consumption of polyunsaturated fatty foods or regularly engage in brisk exercise, etc.)

In another embodiment, behavior health indicator generation logic 116 communicates behavioral health indicator 107 to health tracking device 126 and/or to an online account associated with user 102 so that user 102 might track their current and historical behavioral health indicator 108 just as they might track their activity and/or body metrics via health tracking device or other personal device (e.g., smart phone).

In another embodiment, behavioral health indicator generation logic 116 communications behavioral health indicator 107 to a health sector network 130 associated with, affiliated with, or controlled by one or more health sector providers 128. In one embodiment, health sector network 130 may include de facto health indicator generation logic 132 and composite health indicator generation logic 138. De facto health indicator logic 132 generates de facto health indicator 115 based on health sector data 117. De facto health indicator 115 represents a degree to which the person is observably healthy (i.e., from the perspective of a health sector provider 128). Health sector data 117 may include one or more of (a) health care consumption data representing a degree to which the person has received (or been invoiced for or paid for) health care services from health care providers and (b) health care evaluation data representing results of health care provider-administered examination of the person. In one embodiment, the de facto health indicator 115 is a score based on a separately-calculated consumption health score and a separately-calculated measured health score. Consumption health score may be the quotient of heath consumption (dollars) regarding the persons/health consumption (dollars) for a universe of similarly situated persons (e.g., by age, gender, race, etc.), ranging from 0 to 100, where 0 represents no consumption of health care services and 100 represents the most consumption of health care services.

Similarly, measured health score may be a weighted sum of the following variables obtained from one or more health care provider-administered examinations of a person: blood pressure, lipid profile, body mass index, fasting glucose level, chronic score, and major incident score (e.g., heart attack stroke, etc.), where each variable is normalized to a universe of similarly situated persons (e.g., age, gender, race, etc.), where measured health score ranges from 0 to 100, where 0 is most healthy score and 100 is the least healthy score. De facto health indicator 115 may be the sum of the consumption health score and a separately-calculated measured health score divided by 200, where lower scores indicate better overall health. In other embodiments, de facto health indicator 115 uses different methodologies and weighting criteria. In one embodiment, behavioral health indicator generation logic 116 communicates consumer ID data 105 and/or location ID data 111 to de facto health indicator generation logic 132 to identify and/or request specific universe data from health sector providers 128.

De facto heath indicator 115 may be communicated to composite health indicator generation logic 138 and/or to health sector providers 128, health tracking device 126, and/or an online account associated with user 102. Composite health indicator generation logic 138 generates composite health indicator 121 based on behavioral health indicator 107 and de facto health indicator 115. Because composite health indicator 121 is based not just on de facto health indicator 115 or behavioral health indicator 107, it provides a more complete and accurate depiction of one's current and future health. Composite health indicator 121 may be communicated to health sector providers 128, health tracking device 126, and/or an online account associated with user 102.

In one embodiment, de facto health indicator generation logic 132 includes biasing logic 134 that generates biasing data 119 based on consumer ID data 105 and location ID data 111. Biasing data 119 can be used to bias health sector data 117 and/or behavior health indicator 107 as may be desired (e.g., to account for the location of the person, the marital status of the person, the genetic pre-disposition to certain illness of the person, etc.). In one embodiment, biasing data 119 may be generated by querying biasing database 136 based on one or more of consumer ID data 105 and location ID data 111.

In one embodiment, the generation of behavioral health indicator 107, de facto health indicator 115, and composite health indicator 121, the manner in which behavioral health indicator 107, de facto health indicator 115, and composite health indicator 121 is generated (e.g., what data/information is considered), and the disclosure of behavioral health indicator 107, de facto health indicator 115, and composite health indicator 121 is based on the user's 102 proactive consent and decision. In one embodiment, electronic payments authorization network 108 may include privacy logic 140 that generates privacy control data 125 that controls each of the foregoing based on opt-in request data 123 from user 102. Opt-in request data 123 may be generated in response to a user 102 logging in to a graphical user interface associated with their payment mechanism (e.g., payment card) and granting consent on each or some of the foregoing. Similarly, user 102 may configure settings in their heath tracking device 126 to control the same and consent to the tracking and disclosure of activity data and body metrics data 113. User 102 can withdraw their consent or change their consent as to any or all of the foregoing in the same manner. In one embodiment, personally identifiable information is removed from any disclosure of behavioral health indicator 107, de facto health indicator 115 and composite health indicator 121 prior to disclosure (e.g., to third parties) so that indicator 107, indicator 115, and/or indicator 121 cannot be traced back to a particular user 102.

In one embodiment, each of the indicators 107, 115, and 121 are scores that are capable of being displayed in connection with a health tracking device 126 or a graphical user interface associated with a user 102 account that tracks health data, a health sector provider 128, and/or electronic payments authorization network 108. The specific score or indication preferably provides tangible and meaningful information to the consumer of that information (e.g., the user 102, the health sector provider 128, and/or the payment card companies associated with electronic payments authorization network 108 so that such consumers can react and make decisions based on such indicators 107, 115, and 121.

Although various logic components were described above as being included within electronic payments authorization network 108 or health sector network 130 in one embodiment, those logic components may be separate, distinct and unrelated from such networks 108, 130 and/or included as part of other networks in other embodiments.

Figure 3:
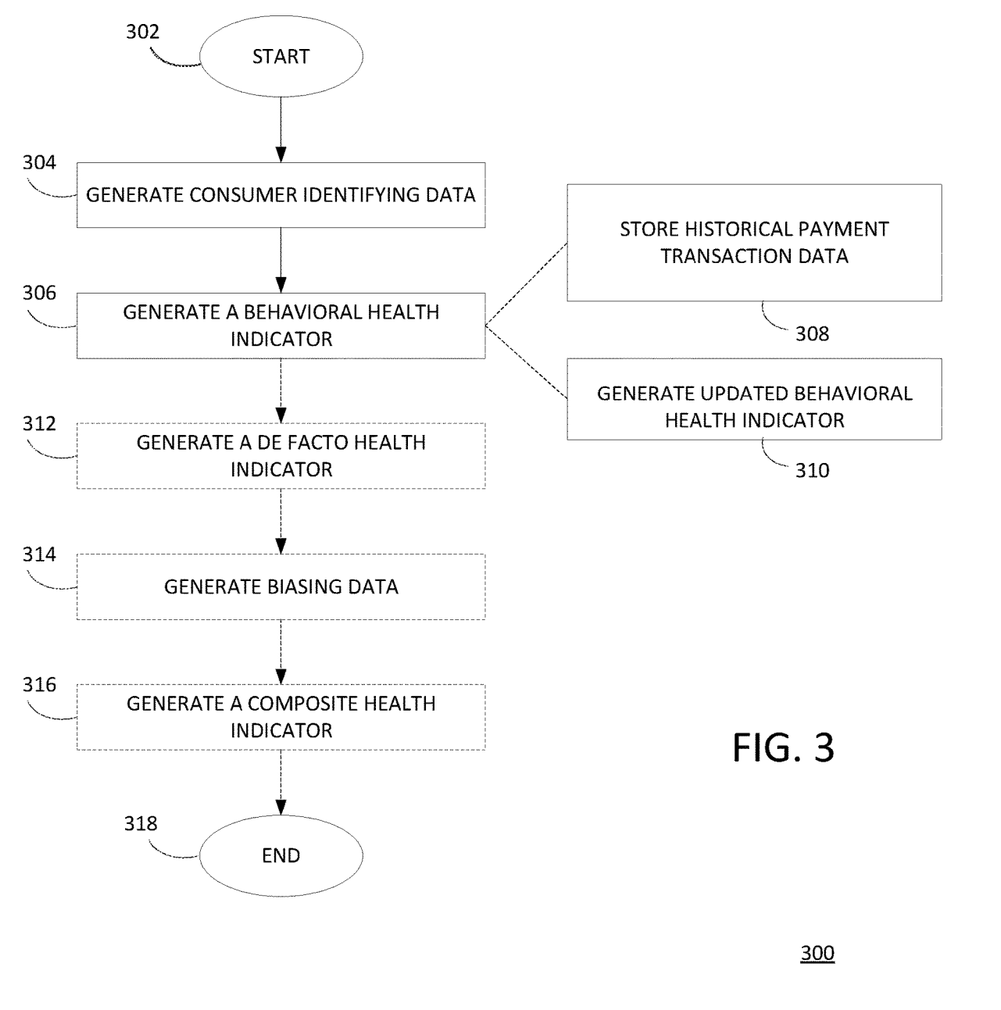
FIG. 3 is a flow chart depicting an exemplary method of using the apparatus of FIG. 1 or FIG. 2 in accordance with one embodiment of the present disclosure.

FIG. 3 depicts an exemplary method 300 of using the apparatus of FIG. 1 and/or FIG. 2 in accordance with one embodiment of the present disclosure. The method 300 starts in block 302 where, for example, a user 102 enters into a payment transaction with merchant 104 and merchant 104 and/or merchant acquiring bank 106 generates payment transaction data 103. The method continues in block 304 where consumer identifying data is generated. In one embodiment, consumer identifying data 105 is generated by consumer ID logic 112 based on payment transaction data 103. The method continues in block 306 where a behavioral health indicator is generated. In one embodiment behavioral health indicator 107 is generated by behavioral health indicator generation logic 116 based on payment transaction data 103. In another embodiment, behavioral health indicator 107 is based on purchased items ID data 109, consumer ID data 105, and/or location ID data 111.

In one embodiment block 306 includes block 308 where the payment transaction data and/or the behavioral health indicator is stored, for example, in historical database 124, and block 310 where an updated behavioral health indicator is generated (e.g., by behavioral health indicator generation logic 116 using new payment transaction data and historical payment transaction data and/or historical behavioral health indicator).

The method may continue in block 312 where a de facto heath indicator is generated. In one example de facto health indicator 115 is generated by de facto health indicator generation logic 132 using health sector data 117. The method may also include block 314 where biasing data may be generated. Biasing data 119 may be generated by biasing logic 134 based on consumer ID data 105 and location ID data 111. And the method may also include generating a composite health indicator in block 316. In one embodiment, composite health indicator 121 may be generated by composite health indicator generation logic 138 based on de facto health indicator 115. In another embodiment, composite health indicator 121 may be based on de facto health indicator 115 and biasing data 119. The method concludes in block 316, where for example, the composite health indicator 121 might be communicated to health sector providers 128, health tracking device 126 and/or an account associated with user 102.

The present disclosure provides an unconventional, efficient, and tangible technical solution to a technical problem of providing meaningful health indicator data to a consumer and various third parties (when consent is provided) based on payment transaction data. By generating behavioral health indicators representative of whether a consumer makes health-conscious decisions (e.g., purchasing decisions, activity decisions, etc.) consumers can efficiently monitor their progress toward their health objectives, track and supervise family members (e.g., relatives living away from the home but who use a family payment card) and health care providers can incentivize healthy practices and/or use such indicators to maintain a more robust medical record of the consumer. In addition, the present disclosure requires the transformation of payment transaction data into behavioral health indicators, the transformation of health sector data into de facto health indicators, and the transformation of both behavioral indicators and de facto health indicators into composite health indicators, thereby tying the operation of the functionality of the logic to the logic's ability to process payment transaction data and health sector data. And, the generation of each of the behavioral health indicator, the de facto health indicator, and the composite health indicator, individually and collectively, improve the efficiency and capabilities of health tracking devices and health sector provider networks.

As used herein, the following terms have the meanings described thereto as set forth below. "Logic" may refer to any single or collection of circuit(s), integrated circuit(s), hardware processor(s), processing device(s), transistor(s), non-transitory memory(s), storage devices(s), non-transitory computer readable medium(s), combination logic circuit(s), or any combination of the above that is capable of providing a desired operation(s) or function(s). For example, "logic" may each take the form of a hardware processor executing instructions from one or more non-transitory memories, storage devices, or non-transitory computer readable media, or a dedicated integrated circuit. "Non-transitory memory," "non-transitory computer-readable media," and "storage device" may refer to any suitable internal or external non-transitory, volatile or non-volatile, memory device, memory chip(s), or storage device or chip(s) such as, but not limited to system memory, frame buffer memory, flash memory, random access memory (RAM), read only memory (ROM), a register, a latch, or any combination of the above. A "hardware processor" may refer to one or more dedicated or non-dedicated: hardware micro-processors, hardware micro-controllers, hardware sequencers, hardware micro-sequencers, digital signal hardware processors, hardware processing engines, hardware accelerators, applications specific circuits (ASICs), hardware state machines, programmable logic arrays, any integrated circuit(s), discreet circuit(s), etc. that is/are capable of processing data or information, or any suitable combination(s) thereof. A "processing device" may refer to any number of physical devices that is/are capable of processing (e.g., performing a variety of operations on) information (e.g., information in the form of binary data or carried/represented by any suitable media signal, etc.). For example, a processing device may be a hardware processor capable of executing executable instructions, a desktop computer, a laptop computer, a mobile device, a hand-held device, a server (e.g., a file server, a web server, a program server, or any other server), any other computer, etc. or any combination of the above. An example of a processing device may be a device that includes one or more integrated circuits comprising transistors that are programmed or configured to perform a particular task. "Executable instructions" may refer to software, firmware, programs, instructions or any other suitable instructions or commands capable of being processed by a suitable hardware processor.

What is claimed is:

1. An apparatus comprising:
consumer identification logic operable to generate, based on payment transaction data, consumer ID data that identifies a person associated with a payment mechanism used in a payment transaction to purchase an item;
wherein the payment transaction data is payment card transaction data containing a plurality of data fields including an item data field, wherein the item data field contains a UPC code, global trade item number (GTIN) data or other item-identifying data;
purchased items determination logic operable to ascertain the content of the data in said item data field and to generate purchased items ID data for said item by correlation of said content; and
behavioral health indicator generation logic operable to:
generate, based on the purchased items ID data, a food health indicator when the item is determined to be a food or beverage item, the food health indicator representing a degree to which the item represents a health-conscious purchase;
generate, based on the purchased item ID data, a lifestyle health indicator when the item is determined to be neither a food item nor a beverage item, the lifestyle health indicator representing a degree to which the item is associated with an active lifestyle;
generate, based on one or more of the food behavioral health indicator and the lifestyle behavioral health indicator, a behavioral health indicator for the person, the behavioral health indicator being representative of a degree to which the person makes health-conscious decisions, and
communicate the behavioral health indicator to a health tracking device associated with the person,
wherein each of the consumer identification generation logic and the behavioral health indicator generation logic is implemented using at least one of: a circuit, an integrated circuit, a hardware processor, a processing device, a transistor, a memory, a non-transitory computer readable medium, and a combination logic circuit.

2. The apparatus of claim 1, further comprising a historical database operative to store the payment transaction data as historical payment transaction data, wherein:
the behavioral health indicator generation logic is further operable to generate an updated behavioral health indicator based on new payment transaction data and the historical payment transaction data,
the new payment transaction data represents a new payment transaction to purchase a new item, and
the updated behavioral health indicator represents an updated degree to which the person makes health-conscious decisions.

3. The apparatus of claim 1, further comprising location determination logic operable to generate location ID data based on said payment transaction data, the location ID data identifying the physical location of the payment transaction, wherein:
the food behavioral health indicator is based on one or more of:
the nutritional value of the item;
the size of the item;
the frequency with which the item is purchased by the person;
the physical location of the payment transaction;
a time of the payment transaction; and
a type of merchant where the payment transaction was made;
and
the lifestyle behavioral health indicator is based on one or more of:
the size of the item;
the frequency with which the item is purchased by the person;
the physical location of the payment transaction; and
a type of merchant where the payment transaction was made.

4. The apparatus of claim 1, wherein the behavioral health indicator generation logic further comprises:
activity quality logic operative to generate, based on activity data from the health tracking device, an activity health indicator representing a degree to which an activity level of the person is consistent with health-conscious decisions; and body metric evaluation logic operative to generate, based on body metric data from the health tracking device, a body metric health indicator representing a degree to which a body metric associated with the person is consistent with health-conscious decisions, wherein:
the behavioral health indicator is further generated using one or more of the activity health indicator and the body metric health indicator, and each of the activity quality logic and the body metric evaluation logic is implemented using at least one of: a circuit, an integrated circuit, a hardware processor, a processing device, a transistor, a memory, a non-transitory computer readable medium, and a combination logic circuit.

5. The apparatus of claim 1, wherein the behavioral health indicator is a score.

6. The apparatus of claim 1, further comprising privacy logic operative to generate privacy control data based on opt-in request data, wherein the behavioral health indicator generation logic communicates the behavioral health indicator to third parties based on the privacy control data.

7. The apparatus of claim 1, wherein:
the apparatus is a non-transitory computer readable medium; and
each of the consumer identification logic, the purchased items determination logic, and the behavioral health indicator generation logic is implemented as computer readable instructions stored on the non-transitory computer readable medium and capable of being executed by a hardware processor.

8. An apparatus comprising:
consumer identification logic operable to generate, based on payment transaction data, consumer ID data that identifies a person associated with a payment mechanism used in a payment transactions to purchase an item;
wherein the payment transaction data is payment card transaction data containing a plurality of data fields including an item data field, wherein the item data field contains a UPC code, global trade item number (GTIN) data or other item-identifying data;
purchased items determination logic operable to ascertain the content of the data in said item data field and to generate purchased items ID data for said item by correlation of said content;
behavioral health indicator generation logic operable to:
generate, based on the purchased items ID data, a food health indicator when the item is determined to be a food or beverage item, the food health indicator representing a degree to which the item represents a health-conscious purchase;
generate, based on the purchased item ID data, a lifestyle health indicator when the item is determined to be neither a food item nor a beverage item, the lifestyle health indicator representing a degree to which the item is associated with an active lifestyle; and
generate, based on one or more of the food behavioral health indicator and the lifestyle behavioral health indicator, a behavioral health indicator for the person, the behavioral health indicator being representative of a degree to which the person makes health-conscious decisions;

de facto health indicator generation logic operative to generate a de facto health indicator based on health sector data and the consumer ID data, wherein:
the health sector data includes one or more of (a) health care consumption data representing a degree to which the person has used health care services from health care providers and (b) health care evaluation data representing results of health care provider-administered examination of the person, and
the de facto health indicator represents a degree to which the person is observably healthy; and composite health indicator generation logic operable to:
generate a composite health indicator for the person based on the de facto health indicator and the behavioral health indicator that is representative of a degree to which the person makes health-conscious decisions, and
communicate the composite health indicator to the a health tracking device associated with the person, wherein each of the consumer identification generation logic, the purchased items determination logic, the behavioral health indicator generation logic, de facto health indicator generation logic, and the composite health indicator generation logic is implemented using at least one of: a circuit, an integrated circuit, a hardware processor, a processing device, a transistor, a memory, a non-transitory computer readable medium, and a combination logic circuit.

9. The apparatus of claim 8, wherein:
the apparatus is a non-transitory computer readable medium; and
each of the de facto health indicator generation logic and the composite health indicator generation logic is implemented as computer readable instructions stored on the non-transitory computer readable medium and capable of being executed by a hardware processor.

10. The apparatus of claim 8, wherein:
the de facto health indicator generation logic comprises biasing logic operable to generate biasing data based on one or more of the consumer ID data and location ID data, wherein the location ID data identifies the physical location of the payment transaction; and
the composite health indicator generation logic weights or adjusts the behavioral health indicator and the de facto health indicator based on the biasing data.

11. A method performed by a hardware processor, the method comprising:
generating, based on payment transaction data, consumer ID data that identifies a person associated with a payment mechanism used in a payment transaction to purchase an item;
wherein the payment transaction data is payment card transaction data containing a plurality of data fields including an item data field, wherein the item data field contains a UPC code, global trade item number (GTIN) data or other item-identifying data;
ascertaining the content of the data in said item data field;
generating purchased items ID data for said item by correlation of said content;
generating, based on the purchased items ID data, a food health indicator when the item is determined to be a food or beverage item, the food health indicator representing a degree to which the item represents a health-conscious purchase;
generating, based on the purchased item ID data, a lifestyle health indicator when the item is determined to be neither a food item nor a beverage item, the lifestyle health indicator representing a degree to which the item is associated with an active lifestyle, generating, based on one or more of the food behavioral health indicator and the lifestyle behavioral health indicator, a behavioral health indicator for the one or more persons, the behavioral health indicator being representative of a degree to which the one or more persons make health-conscious decisions; and communicating the behavioral health indicator to a health tracking device associated with the person.

12. The method of claim 11, the method further comprising:

storing the payment transaction data as historical payment transaction data; and generating an updated behavioral health indicator based on new payment transaction data and the historical payment transaction data, wherein:

the new payment transaction data represents a new payment transaction to purchase a new item, and the updated behavioral health indicator is representative of an updated degree to which the person makes health-conscious decisions.

13. The method of claim 11, wherein generating the behavioral health indicator further includes:

generating, based on activity data from the health tracking device, an activity health indicator representing a degree to which an activity level of the person is consistent with health-conscious decisions; and generating, based on body metric data from the health tracking device, a body metric health indicator representing a degree to which a body metric associated with the person is consistent with health-conscious decisions.

14. The method of claim 11, wherein the behavioral health indicator is a score.

15. A method performed by a hardware processor, the method comprising:

generating, based on payment transaction data, consumer ID data that identifies a person associated with a payment mechanism used in a payment transactions to purchase an item;

wherein the payment transaction data is payment card transaction data containing a plurality of data fields including an item data field, wherein the item data field contains a UPC code, global trade item number (GTIN) data or other item-identifying data;

ascertaining the content of the data in said item data field;

generating purchased items ID data for said item by correlation of said content;

generating, based on the purchased items ID data, a food health indicator when the item is determined to be a food or beverage item, the food health indicator representing a degree to which the item represents a health-conscious purchase;

generating, based on the purchased item ID data, a lifestyle health indicator when the item is determined to be neither a food item nor a beverage item, the lifestyle health indicator representing a degree to which the item is associated with an active lifestyle;

generating, based on one or more of the food behavioral health indicator and the lifestyle behavioral health indicator, a behavioral health indicator for the person, the behavioral health indicator being representative of a degree to which the person makes health-conscious decisions;

generating a de facto health indicator based on health sector data and the consumer ID data, wherein:

the health sector data includes one or more of (a) health care consumption data representing a degree to which the person has used health care services from health care providers and (b) health care evaluation data representing results of health care provider-administered examination of the person, and the de facto health indicator represents a degree to which the person is observably healthy;

generating a composite health indicator for the person based on the de facto health indicator and the behavioral health indicator that is representative of a degree to which the person makes health-conscious decisions; and communicating the composite health indicator to a health tracking device associated with the person.

16. The method of claim 15, further comprising:

generating biasing data based on one or more of consumer ID data and location ID data, wherein the location ID data identifies the physical location of the payment transaction of the one payment transaction; and weighting or adjusting the behavioral health indicator and the de facto health indicator based on the biasing data.

17. The apparatus of claim 8, further comprising:

a historical database operative to store the payment transaction data as historical payment transaction data, wherein:

the behavioral health indicator generation logic is further operable to generate an updated behavioral health indicator based on new payment transaction data and the historical payment transaction data, the new payment transaction data represents a new payment transaction to purchase a new item, and the updated behavioral health indicator is representative of an updated degree to which the person makes health-conscious decisions.

* * * * *